(12) United States Patent
Vogt et al.

(10) Patent No.: US 10,359,157 B2
(45) Date of Patent: Jul. 23, 2019

(54) PHOSPHOR ARRANGEMENT, LASER ACTIVATED REMOTE PHOSPHOR (LARP) SYSTEM AND SPOTLIGHT/HEADLIGHT

(71) Applicant: OSRAM GmbH, Munich (DE)

(72) Inventors: Peter Vogt, Kelheim (DE); Andreas Hammer, Regensburg (DE); Georg Forster, Sinzing (DE)

(73) Assignee: OSRAM GMBH, Munich (DE)

( * ) Notice: Subject to any disclaimer, the term of this patent is extended or adjusted under 35 U.S.C. 154(b) by 0 days.

(21) Appl. No.: 16/052,689

(22) Filed: Aug. 2, 2018

(65) Prior Publication Data
US 2019/0041011 A1 Feb. 7, 2019

(30) Foreign Application Priority Data
Aug. 4, 2017 (DE) .......... 10 2017 213 599

(51) Int. Cl.
| | |
|---|---|
| *F21K 9/64* | (2016.01) |
| *F21S 41/176* | (2018.01) |
| *F21S 41/16* | (2018.01) |
| *F21V 23/04* | (2006.01) |
| *F21Y 115/30* | (2016.01) |
| *G01N 27/20* | (2006.01) |

(52) U.S. Cl.
CPC .............. *F21K 9/64* (2016.08); *F21S 41/16* (2018.01); *F21S 41/176* (2018.01); *F21V 23/0457* (2013.01); *F21Y 2115/30* (2016.08); *G01N 27/20* (2013.01)

(58) Field of Classification Search
CPC ........ F21K 9/64; F21V 23/0457; F21V 25/02; F21V 25/00; F21S 41/16; G01N 27/20; F21Y 2115/30; H01S 5/06825
See application file for complete search history.

(56) References Cited

U.S. PATENT DOCUMENTS

2018/0119897 A1 5/2018 Vogt et al.
2019/0033399 A1* 1/2019 Schmidt ................ G01R 31/44

FOREIGN PATENT DOCUMENTS

DE 102015213460 A1 1/2017
DE 102015220838 A1 4/2017

OTHER PUBLICATIONS

German Search Report based on application No. 102017213599.9 (7 pages) dated Apr. 4, 2018 (Reference Purpose Only).

* cited by examiner

*Primary Examiner* — Joseph L Williams
*Assistant Examiner* — Jose M Diaz
(74) *Attorney, Agent, or Firm* — Viering Jentschura & Partner MBB (57) ABSTRACT

A phosphor arrangement for at least partly converting an excitation radiation is provided. The phosphor arrangement includes a phosphor and a fracture detector used for monitoring the phosphor. The fracture detector includes at least one line track which is operatively connected to the phosphor. The line track extends around the phosphor at least in sections with at least one loop.

15 Claims, 6 Drawing Sheets

Fig. 9

PHOSPHOR ARRANGEMENT, LASER ACTIVATED REMOTE PHOSPHOR (LARP) SYSTEM AND SPOTLIGHT/HEADLIGHT

CROSS-REFERENCE TO RELATED APPLICATION

This application claims priority to German Patent Application Serial No. 10 2017 213 599.9, which was filed Aug. 4, 2017, and is incorporated herein by reference in its entirety.

TECHNICAL FIELD

Various embodiments generally relate to a phosphor arrangement. Furthermore, various embodiments relate to a Laser Activated Remote Phosphor (LARP) system and a spotlight/headlight having a phosphor arrangement.

BACKGROUND

Spotlights/headlights that use Laser Activated Remote Phosphor (LARP) technology are known. In the case of this technology, a conversion element (converter, wavelength conversion element, phosphor arrangement, phosphor element) arranged at a distance from a radiation source and including or consisting of a phosphor is irradiated with an excitation radiation, in particular an excitation beam or pump beam or pump laser beam, in particular with the excitation beam of a laser diode. The excitation radiation is at least partly absorbed by the phosphor and at least partly converted into a conversion radiation or into a conversion light, the wavelengths and hence spectral properties and/or color of which are/is determined by the conversion properties of the phosphor. In the case of down-conversion, the excitation radiation of the radiation source is converted by the irradiated phosphor into conversion radiation having longer wavelengths than the excitation radiation. By way of example, blue excitation radiation, in particular blue laser light, can thus be converted into red and/or green and/or yellow conversion radiation with the aid of the conversion element. In the case of a partial conversion, by way of example, a superimposition of non-converted blue excitation light and yellow conversion light produces white useful light.

A spotlight/headlight having LARP technology includes for example a lighting device having a housing. The laser diode can then be arranged in said housing. A substrate including a phosphor that can be irradiated by the excitation radiation can then be provided between the laser diode and a housing opening. In order to detect cracking at the phosphor, a fracture detector is arranged. Such a fracture detector is disclosed for example in DE 10 2015 213 460. It has an electrically conductive line track arranged on the phosphor. In this case, the line track is connected to an electronic evaluation unit, which can be used to detect in particular a change in resistance at the line track on account of a crack in the phosphor. The temperature-dictated change in the resistance value is concomitantly taken into account here.

SUMMARY

A phosphor arrangement for at least partly converting an excitation radiation is provided. The phosphor arrangement includes a phosphor and a fracture detector used for monitoring the phosphor. The fracture detector includes at least one line track which is operatively connected to the phosphor. The line track extends around the phosphor at least in sections with at least one loop.

BRIEF DESCRIPTION OF THE DRAWINGS

In the drawings, like reference characters generally refer to the same parts throughout the different views. The drawings are not necessarily to scale, emphasis instead generally being placed upon illustrating the principles of the invention. In the following description, various embodiments of the invention are described with reference to the following drawings, in which.

DESCRIPTION

The following detailed description refers to the accompanying drawings that show, by way of illustration, specific details and embodiments in which the invention may be practiced.

Various embodiments provide a phosphor arrangement, an LARP system and a spotlight/headlight which in terms of device technology are configured in a simple fashion and can be used safely.

Various embodiments provide a phosphor arrangement, e.g. for a Laser Activated Remote Phosphor (LARP) e.g. for converting an excitation radiation. Said phosphor arrangement may include an, in particular plate-like, phosphor. Furthermore, a fracture detector can be used for fracture or crack monitoring of the phosphor. The fracture detector preferably has at least one line track or measurement layer which is connected or operatively connected to the phosphor. In various embodiments, the line track extends around the phosphor at least in sections with at least one loop.

This solution has the advantage that the line track connected, e.g. fixedly, to the phosphor is likewise mechanically loaded and/or cracks or cracks apart in the event of a crack of the phosphor. The mechanical loading or damage of the line track can then be detected by an electrical evaluation device on account of a change in the electrical resistance, wherein damage of the phosphor can then consequently also be deduced from the damage or loading of the line track.

A line track is understood to mean e.g. a practically one-dimensionally extended electrical line, that is to say that a longitudinal extend of the line is considerably (in particular by at least a factor of 2, e.g.by at least one order of magnitude) greater than a width and a height. The line track can be e.g. an electrically conductive wire or conductor track incorporated into the phosphor or an electrically conductive wire or conductor track fitted superficially on the phosphor. The conductor track can be embodied as optically nontransparent, for example metallic, or optically transparent, such as in the case of an indium tin oxide (ITO) coating, for example.

In principle, the line track can have an arbitrary shape and generally also be referred to as a line surface. This applies e.g. if a location of cracking that will possibly occur in the future is well known.

Instead of one line track, a plurality or multiplicity of line tracks can be provided, which are electrically contactable for example in each case independently of one another. The configuration of a respective line track is then preferably implemented in accordance with one or more of the aspects mentioned above and below.

In various embodiments, the at least one line track extends at the edge region of the phosphor and/or extends around an, e.g. central, irradiation region of the phosphor. Consequently, a radiation entrance and emergence of radiation into and respectively out of the phosphor can be implemented as necessary to the greatest possible extent independently of the line track. Furthermore, the marginal arrangement of the line track advantageously makes it possible to detect cracking of the phosphor in the edge region, where the highest stresses can occur.

In various embodiments, provision can be made for the line track to extend around the phosphor, e.g. in the edge region or around the irradiation region, in a meandering, e.g. concentric, fashion. By virtue of the meandering configuration, it is possible firstly to cover or extend around a large-area phosphor element region and secondly to form a comparatively thin and long line track, which reacts more sensitively to cracking. In other words, in one configuration, the conductor loop is formed on a surface of the phosphor or in the phosphor and has the shape of a meander, wherein at least one partial loop of the meander extends completely or at least partly around a circular conversion region of the phosphor. Extending partly around can involve extending around to the extent of, for example, greater than 320°, e.g. greater than 330°, e.g. greater than 340°, e.g. greater than 350°, more preferably greater than 355°. In this case, generally provision is also made for the conductor loop to return again by a similar path after a reversal. Such a configuration of the conductor loop guarantees that via the conversion region generally no crack can run from the outer area inward and from the inner area outward, without severing the conductor loop at least once. The same analogously applies to a phosphor arrangement configured in a square, rectangular, polygonal or freeform fashion.

In various embodiments, the line track can be at least partially or substantially completely or completely radially spaced apart from the edge. A marginal free area is thereby provided in order to arrange marginally for example optical elements and/or a mechanical mount. Nevertheless, it is conceivable for contacts of the line track to extend over the edge.

In various embodiments, the phosphor has two large surfaces and an outer edge wall between the large surfaces. The at least one line track preferably extends on one of the large surfaces, as a result of which this is mountable in a simple fashion. It is also conceivable for the line track to extend at least in sections on the edge wall. Consequently, the line track can cover at least parts of the edge wall and prevent a radial emergence of radiation from the phosphor. The phosphor has for example an, in particular approximately, circular cross section, which is preferred for µ-LARP applications. It is also conceivable for the phosphor to have a square, rectangular, polygonal or freeform cross section. A thickness of the phosphor, e.g. as viewed in the direction of the principal optical axis in the case of a transmissive arrangement, can be approximately between 50 and 200 µm, here e.g. approximately 70 µm. The line track has for example a thickness of between approximately 300 and approximately 1000 nm, e.g. 385 nm. By way of example, the phosphor is arranged on an, in particular plate-like, substrate.

In various embodiments, the phosphor arrangement is configured as transmissive, as a result of which it has a coupling-in side and a coupling-out side for the radiation. It is also conceivable to configure the phosphor arrangement as reflective, in which case one side then serves as coupling-in and -out side for the radiation.

In various embodiments, the line track is arranged on a coupling-in side or coupling-out side of the phosphor or alternatively in the phosphor. In various embodiments, it is conceivable for two or more line tracks to be provided. Consequently, by way of example, one line track can be provided at the coupling-in side, and one line track at the coupling-out side. It is also conceivable for one line track to be provided at the coupling-in side or coupling-out side and a further line track to be provided in the phosphor. If at least three line tracks are provided, then one can be provided at the coupling-in side, one at the coupling-out side and one in the phosphor.

The line track may extend on the large surface and/or the edge wall of the phosphor and/or on the substrate. In various embodiments, the line track has one or two end sections arranged on the substrate, said end sections being configured as contact pad(s). As a result, the line track can be contacted in a simple manner in terms of device technology, without the need for additional contact pads to be formed. The contact pads can be arranged for example diametrically with respect to one another in order to achieve a safe distance between the contact pads. It is alternatively conceivable to arrange the contact pads alongside one another, which leads to space-saving contacting.

In various embodiments, provision can be made for at least one end section of the line track to extend radially above the phosphor onto the substrate. The at least one end section can then be formed on the substrate as a contact pad. Furthermore, it is conceivable for at least one end section to extend in particular approximately along a circle arc at the transition region between substrate and phosphor. If two end sections are provided, then it is conceivable for said end sections together to form an approximately closed circle arc, wherein they are spaced apart from one another or at least electrically isolated from one another. The configuration of at least one end section in the shape of a circle arc may be provided in regions in which e.g. a radial emergence of radiation from the phosphor is intended to be prevented. A shielding is thus provided in a simple manner.

In various embodiments, it is conceivable for the line track to be configured in a bifilar fashion and to extend helically, for example. In this case, the line track extends for example in a simple manner helically proceeding from its end sections radially from the outer area toward the inner area of the phosphor. The line track can thus be contacted marginally. It is also conceivable for the line track to extend helically proceeding from its end sections from the radially inner area radially outward, wherein a contacting can then be effected indeed radially at the inner area.

In various embodiments, in a further configuration, a radially inner track section, e.g. a line track configured in a bifilar fashion, extends, e.g. concentrically, circumferentially around the irradiation region. The inner track section can thus form a surround of the phosphor and thereby act as a diaphragm or diaphragm edge in a simple manner in terms of device technology. Consequently, the fracture detector does not just serve for monitoring the phosphor, but can be used as an additional function as a diaphragm. A diaphragm diameter can then be defined for example by the width of the inner track section. In various embodiments, the width of the inner track section is widened or increased in comparison with the rest of the line track.

In various embodiments, a turning loop can be provided, e.g. in the case of the line track configured in a bifilar fashion. The turning loop is then provided e.g. radially at the inner area.

It is also conceivable for end sections to mutually extend one behind another on the phosphor, as a result of which the contacting regions can be arranged offset with respect to one another as viewed in a radial direction.

A distance between sections of the, in particular meandering, line tack which extend approximately parallel may be greater than a track width of the line track, as a result of which the line track constitutes a comparatively small radiation obstacle and in which case larger tolerances are made possible during mounting, without sections which extend parallel touching one another. It is also conceivable for the distance to be smaller than a track width of the line track. By this means, in a simple manner, a large region of the phosphor can be monitored with regard to cracking and a virtually closed diaphragm can be formed as necessary. It is also conceivable for the distance to correspond, e.g. approximately, to a track width of the line track. This results in a good compromise between diaphragm effect and simple production on account of large tolerances.

In various embodiments, the cross section of the line track varies, in particular between the end sections, over its course. In this regard, by way of example, a track section arranged radially at the inner area can be widened, in comparison with the remaining track section lying radially further outward, as a result of which a large-area diaphragm effect is achievable in a simple manner.

In various embodiments, a signal path is provided which electrically connects the line track to an evaluation unit.

In various embodiments, end sections of the line track can be provided on the phosphor, which are then electrically contacted via a respective line, which can be configured e.g. as a contact wheel. Consequently, it is not necessary for the end sections to extend over the edge of the phosphor as far as onto the substrate, wherein the fracture detector is able to be configured extremely compactly and structural space for optical elements, such as a diaphragm, for example, is provided. A respective line can then be contacted with a respective contact pad which is provided on a substrate and via which a simple contacting, e.g. with the signal path, is then made possible.

In various embodiments, end sections of the line track are arranged radially at the outer area or radially at the inner area. It is also conceivable to provide one end section radially at the outer area and one end section radially at the inner area.

In various embodiments, it is conceivable for the end sections of the line track to be spaced apart from one another in a circumferential direction, e.g. to be configured as approximately diametrically opposite, and/or for the, e.g. bifilar, line track to include at least two turning loops. This results in a large-area covering of the phosphor by means of the line track in a simple manner.

In various embodiments, the line track and/or an enclosure element extend(s) around the edge wall of the phosphor. If an enclosure element is provided, then this can prevent emergence of e.g. marginal radiation from the phosphor. The enclosure element can be configured for example as an, e.g. additional, line track or without a detection function. In a simple manner in terms of device technology provision can be made for the enclosure element to be formed from the same material as the line track. Consequently, the enclosure element can be applied, in particular by sputtering, together with the line track or at least by the same method. The enclosure element has for example a ring surface that extends over or on a large surface of the phosphor. Alternatively or additionally, provision can be made for the enclosure element to have a lateral surface extending around the edge wall of the phosphor. Furthermore, alternatively or additionally provision can be made for the enclosure element to have a ring surface which is arranged on the substrate and extends around the phosphor. Two or more of these surfaces can then be connected to one another, e.g. integrally. It is also conceivable for the enclosure element to have one or more slots in order to form one or more line tracks therefrom.

The enclosure element and/or the at least one line track can be configured at least in sections or substantially completely or completely as an antireflection coating and/or as a dichroic coating or have a coating of this type. This can be provided in addition or as an alternative to an antireflection coating and/or dichroitic coating of the phosphor. Consequently, in a simple manner in terms of device technology, the enclosure element and/or the at least one line track can have additional technical functionalities, which makes it possible to save component parts on the phosphor arrangement. A dichroic coating applied to the irradiation surface facing an excitation radiation source can transmit the excitation radiation and reflect the conversion radiation, for example. It is also possible to provide different sections having different antireflection coatings and/or dichroic coatings, for example depending on what excitation wavelength of the respective illuminant is used and on which phosphor arrangement surface the coating is formed.

In various embodiments, it is conceivable for the at least one line track, e.g. as viewed in the direction of the principal optical axis, to extend over different planes in the phosphor.

The at least one line track can be formed from an electrically conductive material, for example. Furthermore, it is conceivable to form the line track at least in sections or completely from an optically transparent or radiation-transmissive material, in order not to disturb radiation concerning the phosphor. Furthermore, it is conceivable to form the line track at least in sections or completely from an optically nontransparent or radiation-nontransmissive material in order for example additionally to use said line track as a diaphragm. By way of example, aluminum, copper, gold or silver can be provided as optically nontransparent material for the line track. The material can be embodied as a layer stack of different materials. By way of example, an indium tin oxide (ITO) can be used as optically transparent material.

It is also conceivable to form the at least one line track at least in sections or completely as a Koch curve and/or at least in sections or completely in the form of a Sierpinski triangle and/or at least in sections or completely in the form of a Mandelbrot set. This has the effect that the phosphor is enclosed over the largest possible area by the line track in predetermined regions.

Various embodiments provide a Laser Activated Remote Phosphor (LARP) system including a radiation source, e.g. a laser diode, for an excitation radiation with the phosphor arrangement according to one or more of the preceding aspects being disposed downstream thereof.

Various embodiments provide a spotlight/headlight including a phosphor arrangement according to one of more of the preceding aspects. The headlight is preferably used in the automotive sector, e.g. in a vehicle.

Further areas of application may be for example spotlights for effect-light lighting systems, entertainment lighting systems, architainment lighting systems, general lighting, medical and therapeutic lighting, lighting systems for horticulture, etc.

The vehicle may be an aircraft or a waterborne vehicle or a landborne vehicle. The landborne vehicle may be a motor vehicle or a rail vehicle or a bicycle. In various embodiments, the vehicle is a truck or an automobile or a motorcycle. The vehicle may furthermore be configured as a non-autonomous or partly autonomous or autonomous vehicle.

Figure 1:
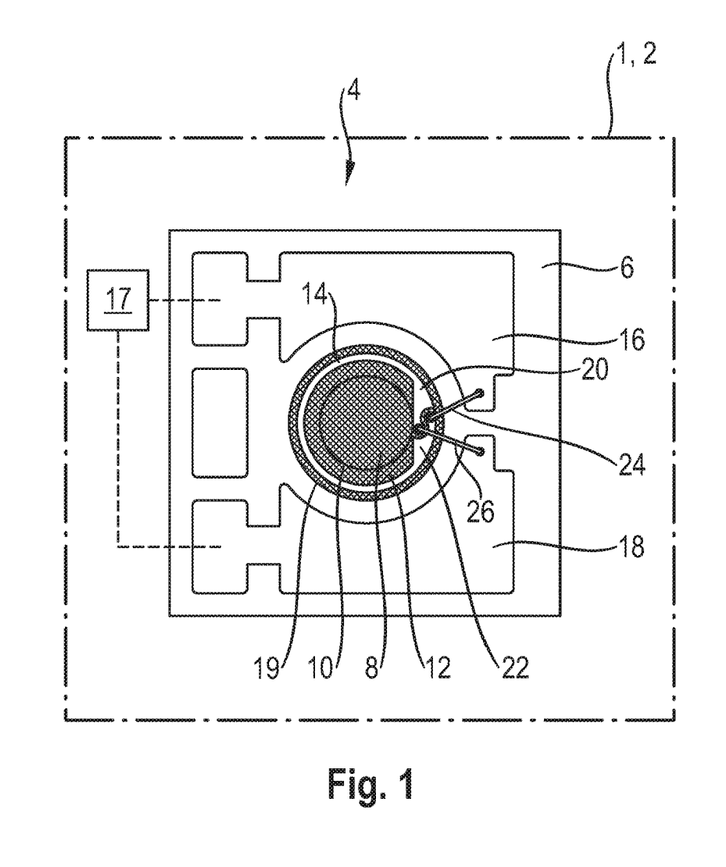
FIGS. 1, 3 to 6, 8 and 9 each show in a plan view a phosphor arrangement in accordance with one embodiment.

In accordance with FIG. 1, a Laser Activated Remote Phosphor (LARP) system 1 of a spotlight/headlight 2 is shown schematically by a dashed line. Said system has a phosphor arrangement 4 including a substrate 6, on which a phosphor 8 is arranged. The phosphor 8 is configured approximately in a circular fashion. Centrally with respect to the phosphor 8, an intended irradiation region 10 is identified by a dashed line. A line track 14 arranged on a large surface 12 of the phosphor 8 extends around the irradiation region 10. Said line track is part of a fracture detector including, besides the line track 14, an evaluation unit, which is electrically connected to the line track 14 via contact pads 16, 18 formed on the substrate 6 on sides of the phosphor 8. An evaluation unit 17 is electrically connected to the contact pad, said evaluation unit being illustrated schematically. The line track 14 is configured approximately in an annular fashion and is spaced apart from the edge 19 of the phosphor 8 and thus offset radially inward. The line track 14 is perforated, as a result of which two end sections 20, 22 are formed. The end sections 20 and 22 are widened in comparison with the rest of the line track 14 and extend one behind another. Via a respective contact wire 24, 26 the end sections 20, 22 or the line track 14 are or is electrically connected to the contact pads 16, 18.

Figure 2:
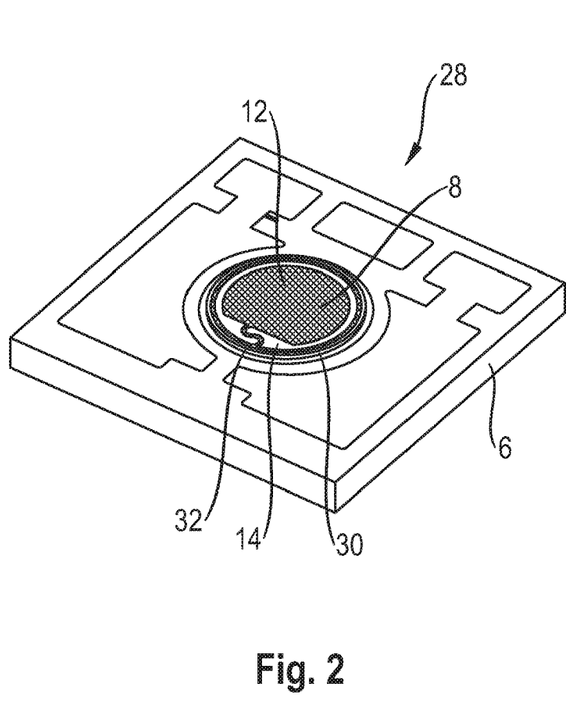
FIG. 2 shows in a perspective illustration a phosphor arrangement in accordance with one embodiment.

In accordance with FIG. 2, in contrast to the embodiment in FIG. 1, a phosphor arrangement 28 is shown in which an enclosure element 30 is provided in addition to the line track 14. Said enclosure element 30 extends around the phosphor 8 marginally and is configured in a closed fashion as viewed in a circumferential direction. Consequently, the enclosure element 30 can prevent radiation from laterally emerging from or entering the phosphor 8. In this case, the ring-shaped enclosure element 30 extends from the large surface 12 over an approximately circular-cylindrical edge wall 32 of the phosphor 8 and joins the substrate 6. for the sake of simplicity, no contact wires for the line track 14 are illustrated in accordance with FIG. 2.

Figure 3:
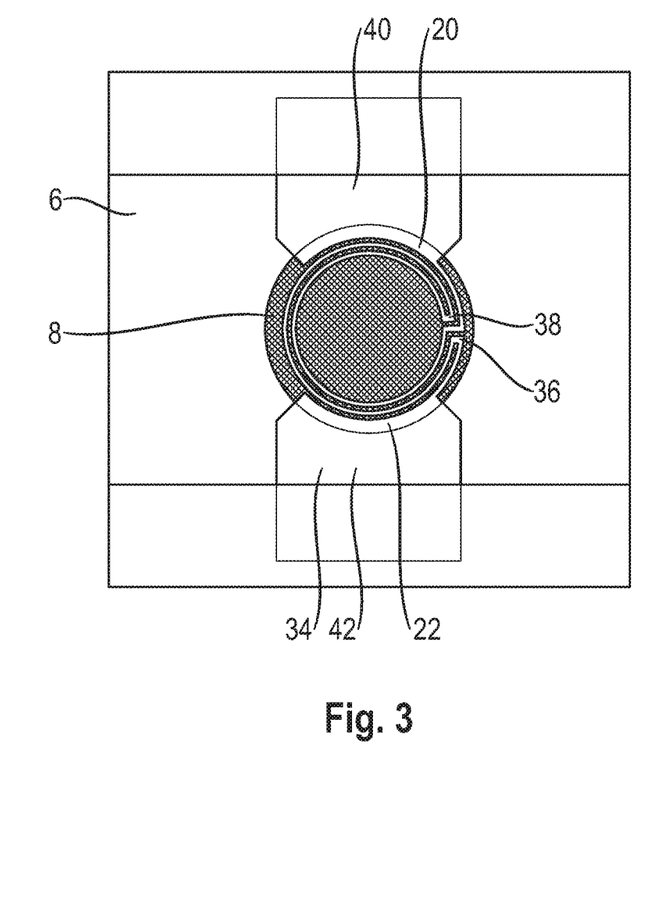

In FIG. 3, in contrast to the previous embodiments, a line track 34 having a different geometric configuration is illustrated. In contrast to the previous embodiments, the line track 34 is configured in a meandering fashion. It is bifilar and extends helically radially inward on the phosphor 8. Proceeding from the first end section 22, the line track 34 extends radially at the outer area and circumferentially as far as a first turning loop 36. Proceeding from the latter, said line track then extends further in the opposite direction and radially further at the inner area circumferentially as far as approximately a region neighboring the first turning loop 36 and forms a second turning loop 38. Proceeding from the latter, the line track 34 extends once again oppositely radially further at the inner area in a circumferential direction approximately as far as the turning loops 36 and 38 and then extends radially between the turning loops 36 and 38 toward the outer area. From there it then runs radially at the outer area further circumferentially as far as the end section 20. The end sections 20 and 22 are arranged in diametrically opposite fashion and extend in each case from the phosphor 8 onto the substrate 6, where they form a respective contact pad 40, 42. The end sections 20, 22 marginally extend over the phosphor 8 on a circle arc encompassing approximately 90°.

Figure 4:
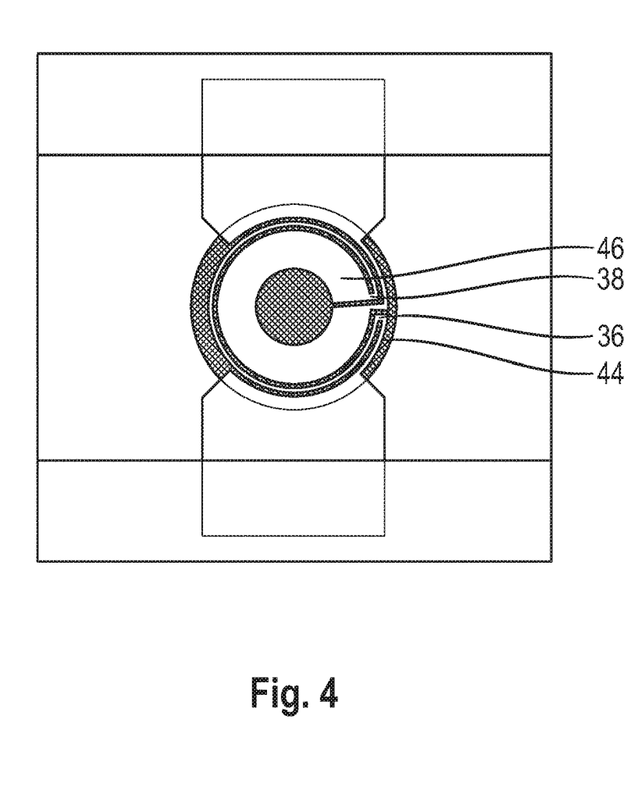

FIG. 4 illustrates a line track 44 in which, in contrast to FIG. 3, an inner line section 46 running between the turning loops 36, 38 is configured as radially widened, whereby a diaphragm is implemented in a simple manner.

Figure 5:
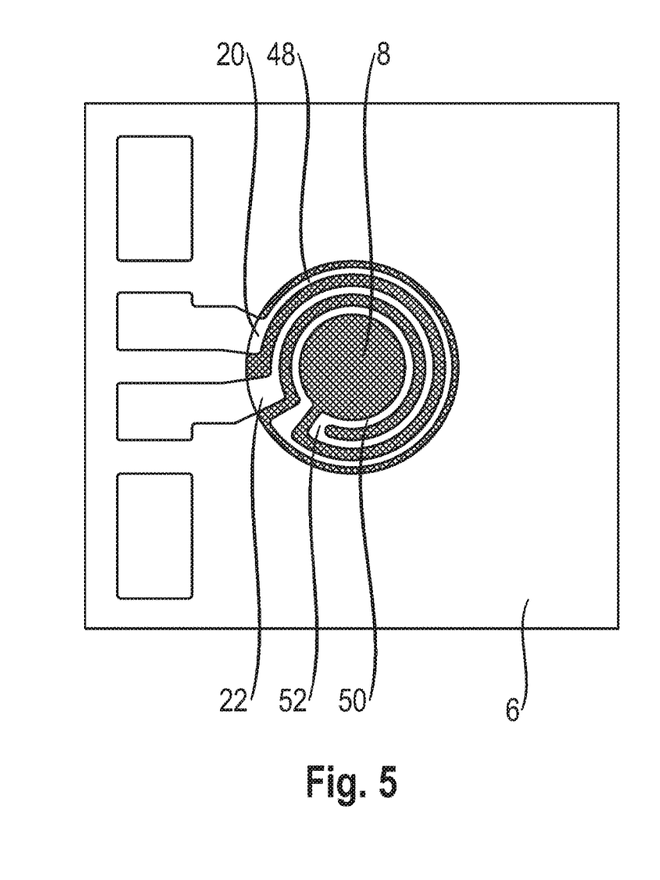

FIG. 5 shows a line track 48 in which end sections 20, 22 are arranged adjacent to one another as viewed in a circumferential direction. In this case, the line track 48 is configured in a bifilar fashion and extends helically radially inward. One inner line section 50 extends almost completely in a circumferential direction. In contrast to the embodiments in accordance with FIG. 3 and FIG. 4, the line track 48 has only one turning loop 52.

Figure 6:
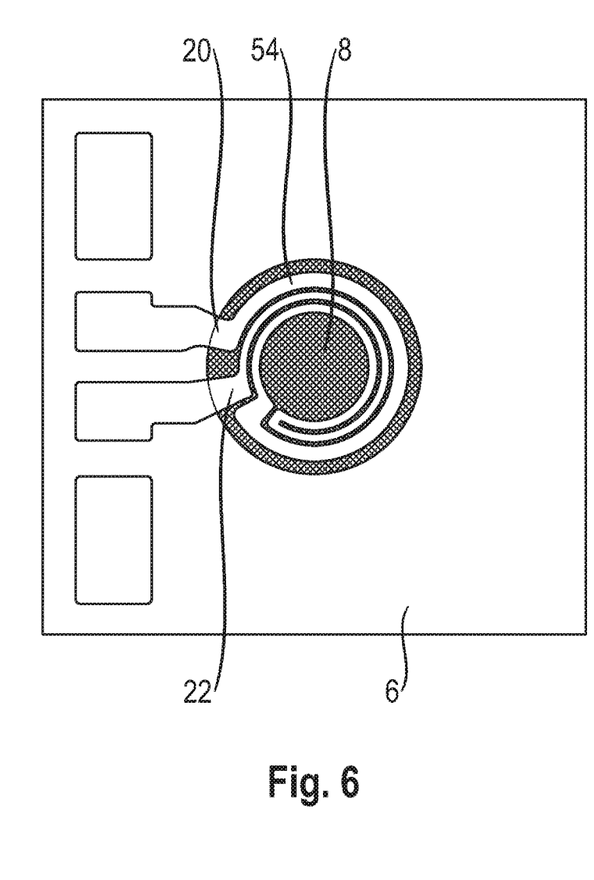

FIG. 6 shows a further embodiment of a line track 54, which is widened in contrast to the embodiment in FIG. 5. The end sections 20, 22 of the embodiments in FIG. 5 and FIG. 6 extend from the phosphor 8 onto the substrate 6 in a manner corresponding to the embodiments in FIG. 3 and FIG. 4.

Figure 7:
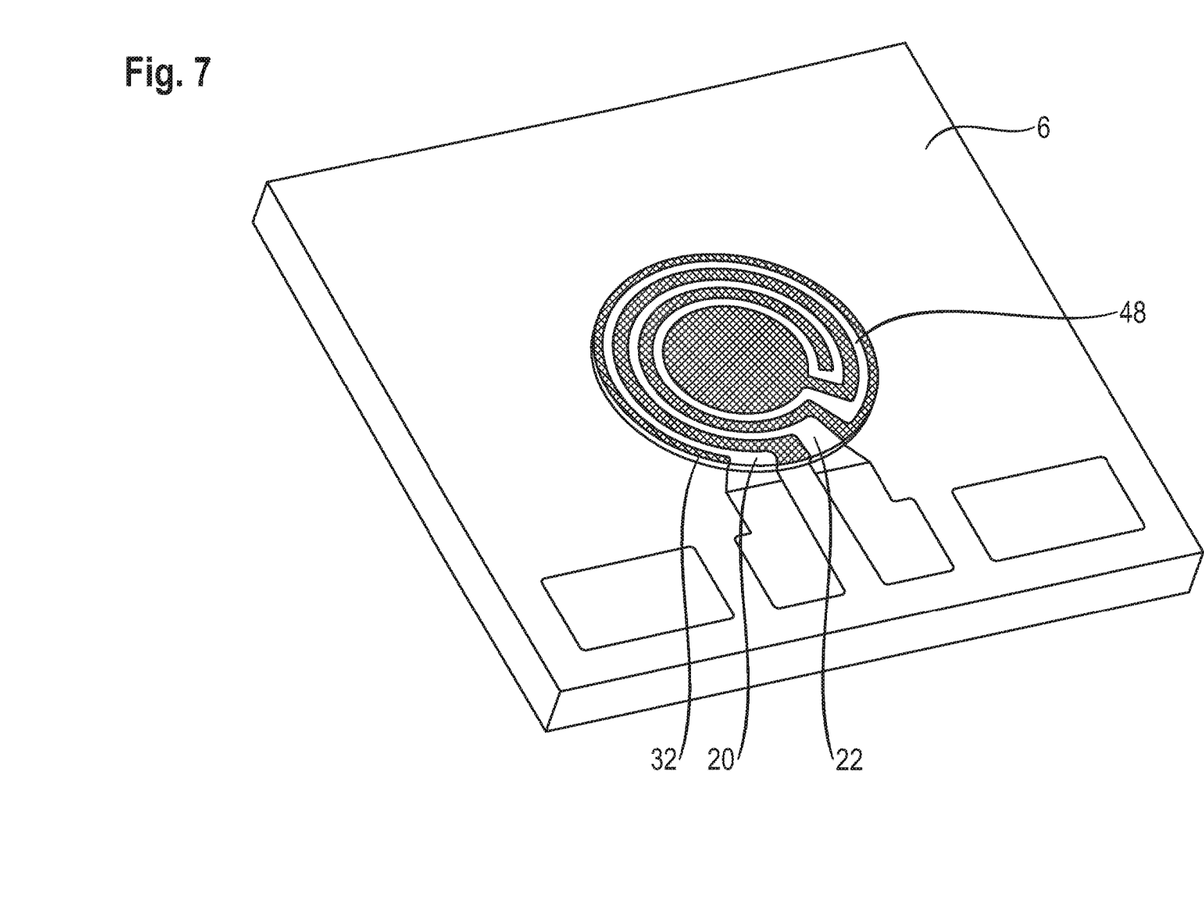
FIG. 7 shows in a perspective illustration the phosphor arrangement in accordance with FIG. 5.

In accordance with FIG. 7, the embodiment from FIG. 5 is shown in a perspective illustration. It is evident that the end sections 20, 22 extend over the edge wall 32 onto the substrate 6.

Figure 8:
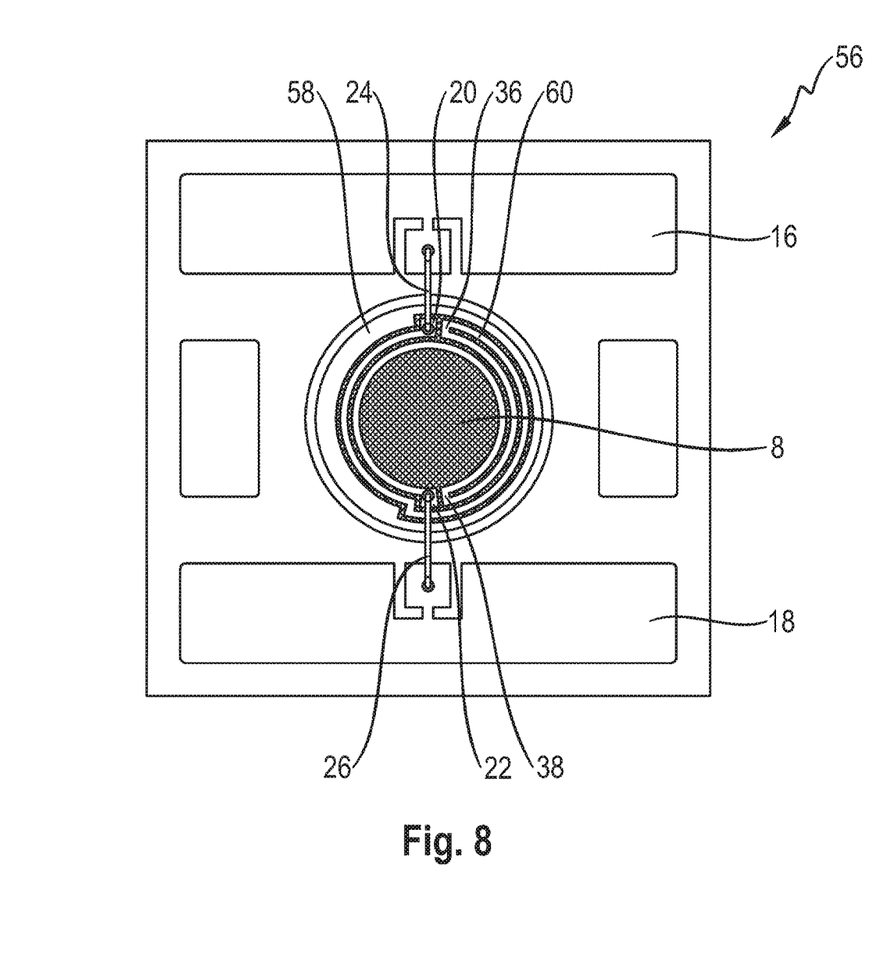

In accordance with FIG. 8, a phosphor arrangement 56 is illustrated, the phosphor 8 of which is enclosed by an enclosure element 58 in a manner corresponding to the embodiment in FIG. 2. A line track 60 is then formed within the enclosure element 58 as viewed in a radial direction. The end sections 20, 22 of said line track are arranged diametrically with respect to one another and are connected to the contact pads 16, 18 via contact wires 24, 26. The line track 60 is configured in a meandering fashion. It extends from the radially outer end section 20 circumferentially approximately once as far as the first turning loop 36 and as far as the end section 20. From the latter it extends radially inward and then in the opposite direction circumferentially for approximately a semicircle as far as the second end section 22. Here the line track 60 then has the second turning loop 38. It then extends once again firstly radially inward and then in the opposite circumferential direction as far as the second end section 22.

Figure 9:
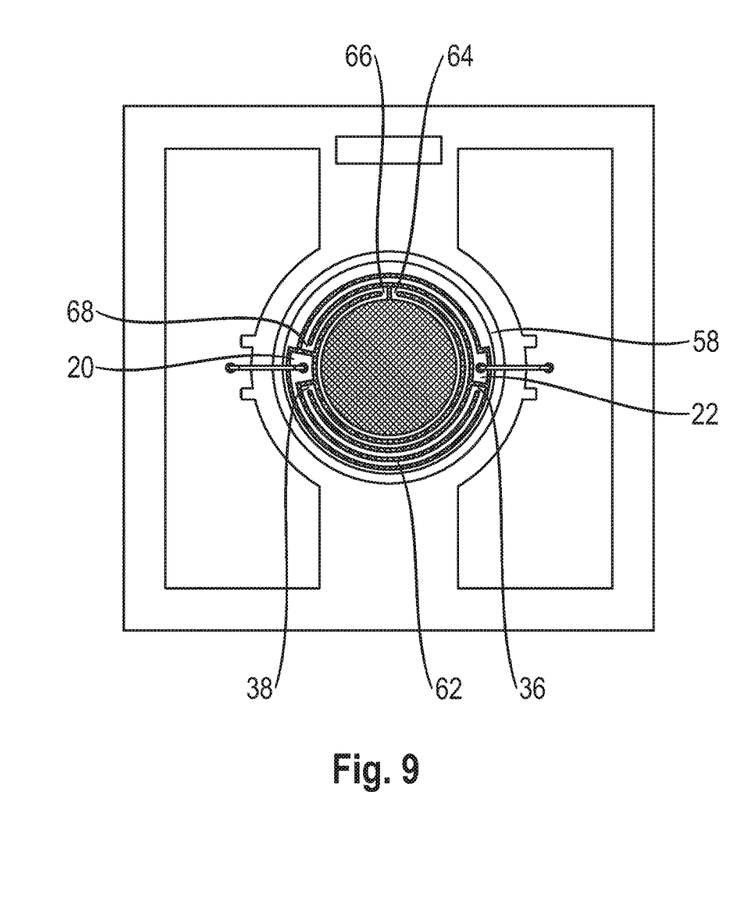

In accordance with FIG. 9 a line track 62 is shown which is configured in a meandering fashion and has an additional turning loop in contrast to the embodiment in FIG. 8. In this case, both end sections 20, 22 are arranged adjacent to the enclosure element 58. Proceeding from the end section 20, the line track extends approximately semicircularly circumferentially as far as the first turning loop 36, which is arranged adjacent to the end section 22. From the latter the line track 62 extends firstly radially inward and then oppositely circumferentially as far as the second turning loop 38, which is formed adjacent to the end section 20. From the latter the line track 62 then extends once again radially inward and then circumferentially approximately for a three-quarter circle as far as a third turning loop 64. It then extends radially inward and then circumferentially for approximately a circle as far as a fourth turning loop 66, which is arranged opposite the turning loop 64. Proceeding from the latter the line track 62 extends radially outward and then circumferentially as far as a fifth turning loop 68, which is provided adjacent to the end section 20. From the turning loop 68 the line track 62 then extends further radially outward and runs circumferentially as far as the other end section 22.

Figure 10:
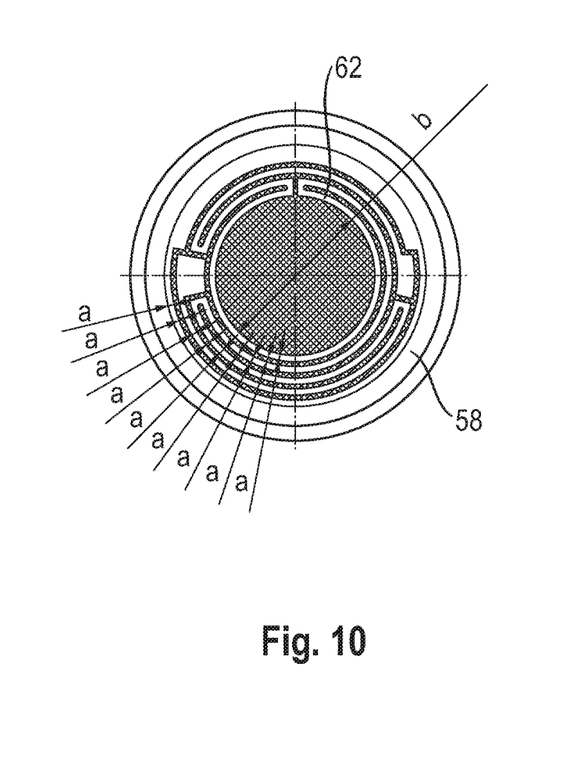
FIG. 10 shows in a plan view the phosphor arrangement from FIG. 9 with dimensioning.

In accordance with FIG. 10, a radial distance a between the sections of the line track 62 with respect to one another and with respect to the enclosure element 58 lies between 0.035 and 0.05 mm. A diameter b of the radially innermost section of the line track 62 is preferably between 1.2 and 1.3 mm.

What is disclosed is a phosphor arrangement including a phosphor having a line track that forms part of a fracture detector. In this case, the line track extends around the phosphor at least in sections.

LIST OF REFERENCE SIGNS

LARP system 1
Spotlight/headlight 2
Phosphor arrangement 4; 28
Substrate 6
Phosphor 8
Irradiation region 10
Large surface 12
Line track 14; 34; 44; 48; 54; 60; 62
Evaluation unit 17
Contact pad 16, 18
Edge 19
End section 20, 22
Contact wire 24, 26
Enclosure element 30; 58
Edge wall 32
Turning loop 36, 38; 52; 64, 66, 68
Contact pad 40, 42
Line section 46; 50
Phosphor arrangement 56

While the invention has been particularly shown and described with reference to specific embodiments, it should be understood by those skilled in the art that various changes in form and detail may be made therein without departing from the spirit and scope of the invention as defined by the appended claims. The scope of the invention is thus indicated by the appended claims and all changes which come within the meaning and range of equivalency of the claims are therefore intended to be embraced.

What is claimed is:

1. A phosphor arrangement for at least partly converting an excitation radiation, the phosphor arrangement comprising:
   a phosphor; and
   a fracture detector used for monitoring the phosphor;
   wherein the fracture detector comprises at least one line track which is operatively connected to the phosphor;
   wherein the line track extends around the phosphor at least in sections with at least one loop.

2. The phosphor arrangement of claim 1,
   wherein the line track is radially spaced apart from the edge of the phosphor.

3. The phosphor arrangement of claim 1,
   wherein the line track is at least one of provided at the edge region of the phosphor or extends around an irradiation region of the phosphor.

4. The phosphor arrangement of claim 1,
   wherein the line track extends around the phosphor at least one in the edge region or around the irradiation region in a meandering and approximately concentric fashion.

5. The phosphor arrangement of claim 1,
   wherein the line track is arranged on at least one of a coupling-in side or a coupling-out side of the phosphor or in the phosphor.

6. The phosphor arrangement of claim 1,
   wherein the line track extends in sections on a substrate provided for the phosphor.

7. The phosphor arrangement of claim 6,
   wherein the line track is arranged on the substrate by one or two end sections, which is/are configured as contact pad(s).

8. The phosphor arrangement of claim 6,
   wherein at least one end section of the line track extends along a circle arc at the transition region between the substrate and the phosphor.

9. The phosphor arrangement of claim 1,
   wherein the line track is configured in a bifilar fashion and extends helically.

10. The phosphor arrangement of claim 1,
    wherein a radially inner track section of the line track extends circumferentially around the irradiation region.

11. The phosphor arrangement of claim 10,
    wherein a width of the inner track section is widened in comparison with the rest of the line track.

12. The phosphor arrangement of claim 1,
    wherein at least one turning loop is provided at the line track.

13. The phosphor arrangement of claim 1,
    wherein at least one of an enclosure element or the line track extend(s) around an edge wall of the phosphor.

14. A Laser Activated Remote Phosphor system, comprising:
    a radiation source comprising a phosphor arrangement disposed downstream of said radiation source;
    wherein the phosphor arrangement comprises:
      a phosphor; and
      a fracture detector used for monitoring the phosphor;
      wherein the fracture detector comprises at least one line track which is operatively connected to the phosphor;
      wherein the line track extends around the phosphor at least in sections with at least one loop.

15. A spotlight/headlight, comprising:
    a phosphor arrangement, comprising:
      a phosphor; and
      a fracture detector used for monitoring the phosphor;
      wherein the fracture detector comprises at least one line track which is operatively connected to the phosphor;
      wherein the line track extends around the phosphor at least in sections with at least one loop.

* * * * *